(12) United States Patent
Jirgal

(10) Patent No.: US 9,488,617 B2
(45) Date of Patent: Nov. 8, 2016

(54) SENSOR DEVICE FOR DETECTING FLOWABLE MEDIA, A PRESSURE DEVICE AND A MEASURING METHOD

(75) Inventor: Matthias Leo Jirgal, Saarbrucken (DE)

(73) Assignee: HYDAC TECHNOLOGY GMBH, Sulzbach/Saar (DE)

( * ) Notice: Subject to any disclaimer, the term of this patent is extended or adjusted under 35 U.S.C. 154(b) by 462 days.

(21) Appl. No.: 13/261,767

(22) PCT Filed: Apr. 26, 2012

(86) PCT No.: PCT/EP2012/001789
§ 371 (c)(1),
(2), (4) Date: Oct. 28, 2013

(87) PCT Pub. No.: WO2012/150013
PCT Pub. Date: Nov. 8, 2012

(65) Prior Publication Data
US 2014/0053640 A1    Feb. 27, 2014

(30) Foreign Application Priority Data
May 5, 2011    (DE) .......................... 10 2011 105 813

(51) Int. Cl.
| | | |
|---|---|---|
| G01N 27/74 | (2006.01) |
| F15B 1/16 | (2006.01) |
| G01F 1/05 | (2006.01) |
| G01F 23/22 | (2006.01) |
| G01F 23/296 | (2006.01) |
| G01M 3/24 | (2006.01) |

(52) U.S. Cl.
CPC ............... *G01N 27/74* (2013.01); *F15B 1/165* (2013.01); *G01F 1/05* (2013.01); *G01F 23/22* (2013.01); *G01F 23/2967* (2013.01); *G01M 3/24* (2013.01); *F15B 2201/50* (2013.01)

(58) Field of Classification Search
CPC ............ F15B 1/08; F15B 1/165; G01F 1/05; G01F 23/22; G01F 23/28; G01F 23/282; G01F 23/284; G01F 23/2845; G01F 23/2967; G01M 3/24; G01N 27/74; H01H 36/00–36/02
See application file for complete search history.

(56) References Cited

U.S. PATENT DOCUMENTS

| | | | | |
|---|---|---|---|---|
| 3,224,250 A | * | 12/1965 | Ming ..................... | G01N 11/16 340/632 |
| 3,368,213 A | | 2/1968 | Quinn | |
| 3,585,622 A | | 6/1971 | Quinn et al. | |
| 4,167,201 A | * | 9/1979 | Zahid ....................... | F15B 1/08 138/30 |
| 4,530,234 A | * | 7/1985 | Cullick .................. | G01N 11/00 73/19.02 |

(Continued)

FOREIGN PATENT DOCUMENTS

| | | |
|---|---|---|
| DE | 26 31 061 A1 | 1/1977 |
| DE | 29 12 618 A1 | 10/1979 |
| DE | 35 00 098 A1 | 7/1985 |
| DE | 10 2009 010 775 A1 | 9/2010 |
| JP | 58 221142 A | 12/1983 |
| JP | 2008190908 A | 8/2008 |

*Primary Examiner* — Minh N Tang
*Assistant Examiner* — David Frederiksen
(74) *Attorney, Agent, or Firm* — Wenderoth, Lind & Ponack, L.L.P.

(57) ABSTRACT

A sensor device (1) detects flowable media (3, 3'), in particular fluids (9) received in pressure devices (5), such as pressure containers (7) or pressure lines. A sensor element (11) has an oscillation device (13) that is excited to produce oscillations under the action of a field (15) of a field generation device (17). The oscillating behavior of the oscillations changes upon inflow of the respective medium (3). The changes can be detected by a measuring device (19).

18 Claims, 2 Drawing Sheets

(56) References Cited

U.S. PATENT DOCUMENTS

| | | |
|---|---|---|
| 4,644,803 A | 2/1987 | Ward |
| 4,788,851 A | 12/1988 | Brault |
| 4,926,015 A * | 5/1990 | Takahashi .............. H01H 36/02 200/84 C |
| 6,244,100 B1 * | 6/2001 | Hastings ................. G01M 3/24 73/40.5 A |
| 2005/0015000 A1 * | 1/2005 | Djennati ............ G01N 33/4905 600/369 |
| 2007/0084282 A1 * | 4/2007 | Hagg .................... G01F 23/284 73/290 R |
| 2008/0204014 A1 * | 8/2008 | Desvaux .............. G01R 33/4608 324/307 |
| 2008/0236685 A1 * | 10/2008 | Nourdine .............. B60K 15/04 137/599.18 |

* cited by examiner

SENSOR DEVICE FOR DETECTING FLOWABLE MEDIA, A PRESSURE DEVICE AND A MEASURING METHOD

FIELD OF THE INVENTION

The invention relates to a sensor device for detecting flowable media, in particular in the form of fluids. Fluids can be received in pressure devices, such as pressure containers or pressure lines. The sensor device has at least one sensor element. The invention further relates to a pressure device, in particular in the form of a pressure container or a pressure line, as well as a measuring method for operating the sensor device in a pressure device.

BACKGROUND OF THE INVENTION

Flowable media, as defined by the present invention, are frequently and especially used in drive technology, for example as a lubricant and/or coolant or as a pressurizing medium in hydraulic systems to transfer energy from a pressurizing medium source to a load. Flowable media are located in pressure devices, such as pressure containers or pressure lines. Pressure containers in particular can fulfill the widest variety of tasks in such hydraulic systems. For example, they may be used for energy storage, the provision of a fluid reserve, the emergency actuation of loads, shock absorption and the like. In addition to knowledge of the physical operating parameters, such as pressure or flow rates in those pressure devices, the safe and proper operation of a hydraulic system requires information about the quality of the flowable media in the hydraulic system or information as well about the presence of flowable media in regions of those pressure devices or in regions of the hydraulic system, respectively.

DE 101 52 777 A1 describes an apparatus for determining the quality of a medium, in particular of a lubricant and/or coolant, having multiple sensors. The sensors emit an electrical output signal as a function of the respective sensor-specific input variable. One sensor is a temperature sensor, which emits an output signal that is essentially only dependent on the temperature of the medium and in particular, is essentially independent of the quality of the medium. An additional sensor emits an output signal that is dependent both on the quality of the medium and on the temperature of the medium. The sensors used are disposed on a common substrate that can be submerged in the respective medium that is to be tested. The apparatus formed in this way permits determining the quality-determining parameters of flowing media independent of the current temperature of said media.

DE 10 2009 010 775 A1 describes a pressure device in the form of a hydraulic accumulator for accommodating at least a partial volume of pressurized fluid, in particular a hydropneumatic accumulator. The hydraulic accumulator has a housing having at least one connection point for connecting the hydraulic accumulator to a hydraulic device. Data memory is a component of the hydraulic accumulator such that the data saved to the data memory can be read electronically by a reading and/or writing device disposed outside the hydraulic accumulator. The operating condition of the hydraulic accumulator can thereby be reliably determined and monitored, preferably can also be carried out in an automated manner, and can be controlled by a control device.

If a sensor device is only used to detect the presence of flowable media in pressure devices of hydraulic systems and/or the type of flowable medium present, these known sensor devices present costly and complex solutions for this application.

DE 35 00 098 A1 discloses a sensor device conforming to its genre for detecting flowable media, in particular in the form of fluids, which can be received in pressure devices such as pressure containers or pressure lines. The sensing device has at least one sensor element. That sensor element has an oscillation device, which is excited to produce oscillations under the influence of a magnetic field of a field generation device. The oscillation behavior of those oscillations changes upon the influx of the respective medium. That the change can be detected by a measuring device. The field generation device is formed by a magnetic device. The measuring device is formed by at least one electromagnetic solenoid. In addition to an electrical voltage in the solenoid, the magnetic flux of the electromagnetic solenoid is influenced by the oscillations of the sensor element when that sensor element is excited.

The known solution has a complicated design and is, therefore, expensive and difficult to produce.

SUMMARY OF THE INVENTION

An object of the invention is to provide an improved sensor device for detecting flowable media, in particular in the form of fluids, which can be received in pressure devices such as pressure containers or pressure lines, with sensing device being cost-effective and easy to produce, and being reliable in operation.

An object of the present invention is also to provide a pressure device, in particular in the form of a pressure container or a pressure line, equipped with a sensor device for detecting flowable media, where its design is cost-effective, simple and robust. A further object of the invention is to provide a suitable measuring method.

These objects are basically achieved by a sensor device, by a pressure device, as well as by a measuring method for operating the sensor device, where the oscillation device of the sensor element is formed in the manner of a reed switch or reed contact. Reed switches of this type can be purchased as inexpensive standard components on the market. Due to their simple structural design, a very good calibration and measurement value setting for measurement tasks, can be achieved by the respective reed device. In addition, the reed device of this type according to the invention can be compactly designed and can easily be accommodated for measurement tasks in the most cramped of installation conditions.

Reed switches and reed contacts preferably have two contact blades enclosed by a casing, preferably in the form of a casing made out of glass, and at the same time form contact springs and a kind of solenoid armature. The contact activation of the contact blades is carried out by a magnetic field acting from the outside and electrically generated by a permanent magnet (reed contact) placed nearby in an associated solenoid coil (reed switch). The two contact blades are drawn towards one another by the effect of the magnetic field. As soon as the magnetic field decreases or a specific field strength is exceeded, the present relative contact of the contact blades opens up again due to the spring action. The contact blades can thereby oscillate freely. The electromagnetic solenoid or the magnetic field thereof, respectively, disposed near the contact blades, is modulated by the contact blades. A signal voltage is thereby generated in the same solenoid.

In an especially preferred exemplary embodiment, the respective reed switch or reed contact is formed of at least two preferably soft magnetic, elastic metal tongues. The tongues move towards or away from one another respectively as the field strength of the magnet device increases or decreases and are excited to produce oscillations. In so doing, at least one oscillation characteristic of the oscillations of the contacts changes upon the influx of the flowable medium, so that the flowable medium can be detected by the measuring and evaluation device. In an especially preferred exemplary embodiment of the sensor device, the measuring and evaluation device detects the absolute number of oscillations of the sensor element or the number of oscillations of the sensor element above a predeterminable threshold value of an oscillation amplitude, preferably as a function of the medium that is to be detected.

The measuring device is connected to the evaluation device, preferably by a data transmission path, which may be formed by a cable connection or radio link, for example. The evaluation device is preferably disposed outside the pressure device, for example, so that it can be connected in the easiest way possible to a display device visible on the outside. A radio link is understood here to mean, in particular, a connection of the measuring device to the evaluation device by electromagnetic waves.

The respective sensor element has an oscillation device, which is excited to produce oscillations under the influence of a field of a field generation device, the oscillation behavior of which oscillations changes upon the influx of the respective medium to be detected. These changes can be detected by a measuring device for subsequent evaluation. This device has the advantageous effect to permit detection of the presence and the kind of flowable medium in the simplest way possible, preferably in a pressure device of any design. The detection of flowable media can be used here in particular as a prerequisite for the use of safety functions or the control of operating procedures, even in pressure devices having a complex design.

In an especially preferred exemplary embodiment of the sensor device, the field generation device is formed by a magnetic device, and the measuring device is formed by at least one electromagnetic solenoid. In addition to an electrical voltage in the solenoid, the magnetic flux of the electromagnetic solenoid is influenced by the oscillations of the sensor element when that sensor element is excited. Preferably, the sensor element behaves here like a mechanical oscillator. A mechanical oscillator is defined in that this oscillator is brought out of static balance through the input of energy and subsequently released to obtain at least one oscillation, preferably to obtain a plurality of oscillations. A continuous conversion of energy takes place due to the oscillation process thus initiated.

In an especially preferred exemplary embodiment of the sensor device, the field generation device and the measuring device are combined to form a single component, preferably in the form of the electromagnetic solenoid. In this way, an especially compact and cost-effective sensor device can be built, which can be incorporated in even the smallest pressure devices and used there for the detection of flowable media. The electromagnetic solenoid thus serves both as an actuator and as a sensor. This solenoid excites the sensor element to perform oscillations. Also a signal voltage is induced in the electromagnetic solenoid by the sensor element due to the modulation of the electromagnetic field of the electromagnetic solenoid by the sensor element.

To allow the flowable medium to be detected to reach the sensor element, the sensor element has a casing, preferably made out of a plastic or glass material, in which at least one opening is located for the influx of the flowable medium. A single opening in the casing of the sensor element is sufficient. Preferably, at least two openings are present. The respective opening is preferably formed such that the result is a capillary action of the flowable medium. By the capillary action, the flowable medium is drawn through the opening into the interior of the casing and towards the sensor element.

The energy for the operation of the sensor element and/or of the measuring device is preferably obtained from an electrical energy source such as an accumulator, for example in the form of a battery, or is obtained through an inductive coupling of the sensor element and the measuring device with an energy source of the evaluation device or from energy of the medium within the pressure device. In this case, the difference in electrical potentials, the temperature differences and the relative speed between the sensor element and the flowing medium can be made use of, or energy can be obtained from pressure fluctuations in the medium. The supply of electrical energy from an electrical energy source to the sensor element and/or the measuring device can be obtained via an electrical feed line, which may be designed as a single-phase power supply, insofar as the device is used as a second electrode. The provision of energy for the operation of the sensor element and/or the measuring device from temperature differences in the flowable medium that is to be detected is preferably obtained by utilizing the Seebeck effect, for example by using a thermoelectric generator.

By a sensor device according to the invention, at least one flowable medium located in the pressure device can be detected, or an absence of such a flowable medium can be determined in a pressure device, in particular in the form of a pressure container or of a pressure line. In accordance with the sensor device according to the invention, a medium present in a media mixture (solution, suspension) and/or at least one medium flow can also be detected. In so doing, the respective pressure device can also be kept unpressurized or a vacuum may be applied thereto.

In this case, an evaluation device of the sensor device can be disposed on the sensor element of the pressure device. Advantageously, the evaluation device is disposed outside the pressure device. This evaluation device can be connected to the sensor element with the aid of a data transmission path of the sensor device, preferably in the form of a cable connection or radio link. A unipolar or multipolar cable connection is suitable as a cable connection. However, advantageously a wireless data transmission path in the form of a radio link can be used, with the aid of data transmission by radio waves, for example having a frequency of more than 100 MHz. This arrangement will result in a range of several meters with a corresponding transmission power and/or suitable frequency ranges.

To use the sensor device, a pressure device can be provided in the form of a hydraulic accumulator, for example in the form of a bellows accumulator, a membrane accumulator, a piston accumulator or a bladder accumulator, having at least one separator disposed in the accumulator housing of the hydraulic accumulator and preferably movably disposed. The separator separates two adjacently disposed media chambers within the accumulator housing, containing different media, from one another.

The sensor device is then disposed in at least one media chamber of the accumulator to detect an inadvertent media inflow into this chamber, which periodically provides an indication of the current operating state of the hydraulic accumulator, for example by determining that the separator has a point of failure in the form of a tear, break or the like. The result of the separator failure is that the one medium (hydraulic oil) has flowed from its originating media chamber, through the separator into the other media chamber with the medium (nitrogen gas) therein to impact the working and energy storage capacity. In some cases this separator failure can also lead to a complete failure of the hydraulic accumulator.

Such a failure is then signaled by the evaluation device, for example, to maintenance or operating personnel to initiate appropriate measures such as repairs or the replacement of the hydraulic accumulator. Depending on the overall size of the mechanical oscillator in use, the inadvertent infiltration of even the smallest amounts of foreign media into the separated media chamber containing the other medium can be reliably detected. Constant monitoring of the functional status of a pressure device is thereby readily possible with the aid of the sensor device according to the invention.

In an especially advantageous exemplary embodiment, a measuring method for operating the sensor device according to the invention has a nominal value compensation, for example, carried out by the measuring and evaluation device. The nominal value compensation accounts for a current pressure in the media chamber, in which the sensor element is mounted, and for a current temperature in at least one of the media chambers, which improves the reliability of the method.

Other objects, advantages and salient features of the present invention will become apparent from the following detailed description, which, taken in conjunction with the drawings, discloses a preferred embodiment of the present invention.

BRIEF DESCRIPTION OF THE DRAWINGS

Referring to the drawings that form a part of this disclosure.

DETAILED DESCRIPTION OF THE INVENTION

Figure 1:
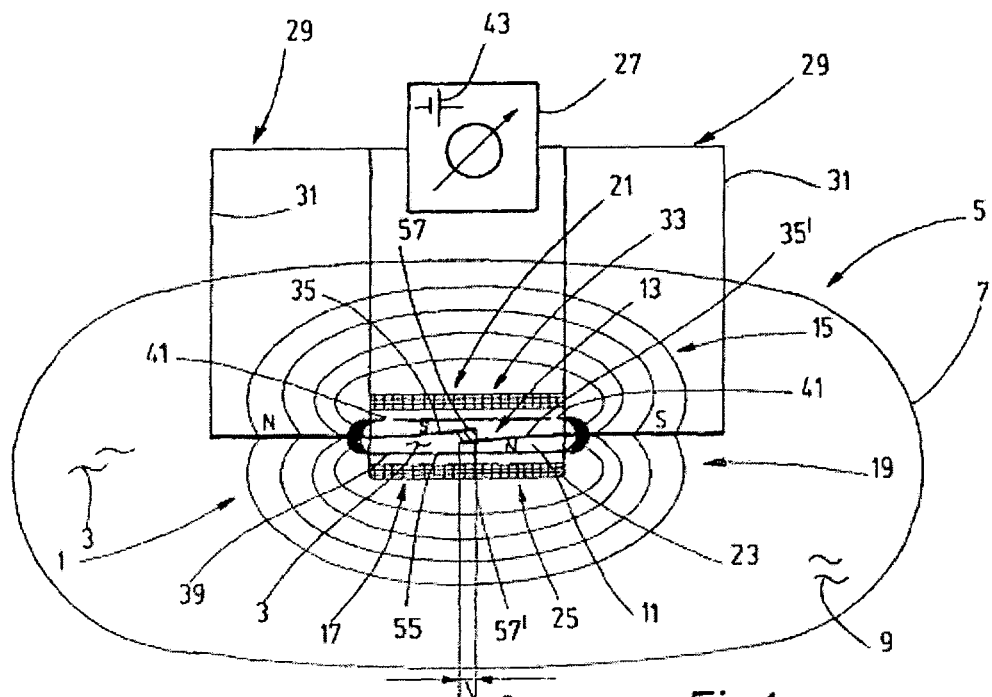
FIG. 1 is a schematic diagram of a sensor device according to an exemplary embodiment of the invention together with an evaluation device.

FIG. 1 shows, in the form of a schematic diagram, a sensor device 1 for detecting flowable media 3, in particular in the form of fluids or liquids 9, which can be received in pressure devices 5 such as pressure containers 7 or pressure lines, having at least one sensor element 11. The sensor element 11 has an oscillation device 13, which is excited to produce oscillations under the influence of a field 15 of a field generation device 17 (cf. FIG. 2). The oscillation behavior of the oscillation device 13 changes upon the influx of the respective flowable medium 3. The change in the oscillation behavior of the oscillation device 13 is detected by a measuring device 19. In the exemplary embodiment of the sensor device 1 according to the invention shown in FIG. 1, the field generation device 17 is formed by a magnetic device 21, and the measuring device 19 is formed by at least one electromagnetic solenoid 23. The magnetic flux of the electromagnetic solenoid 23 and an electrical voltage in the solenoid 23 are influenced by the oscillations of the sensor element 11 excited by the electromagnetic solenoid 23.

As FIG. 1 in particular shows, in an especially preferred exemplary embodiment of the sensor device, the field generation device 17 and the measuring device 19 are combined to form a single component 25, in this case in the form of the electromagnetic solenoid 23.

Figure 3:
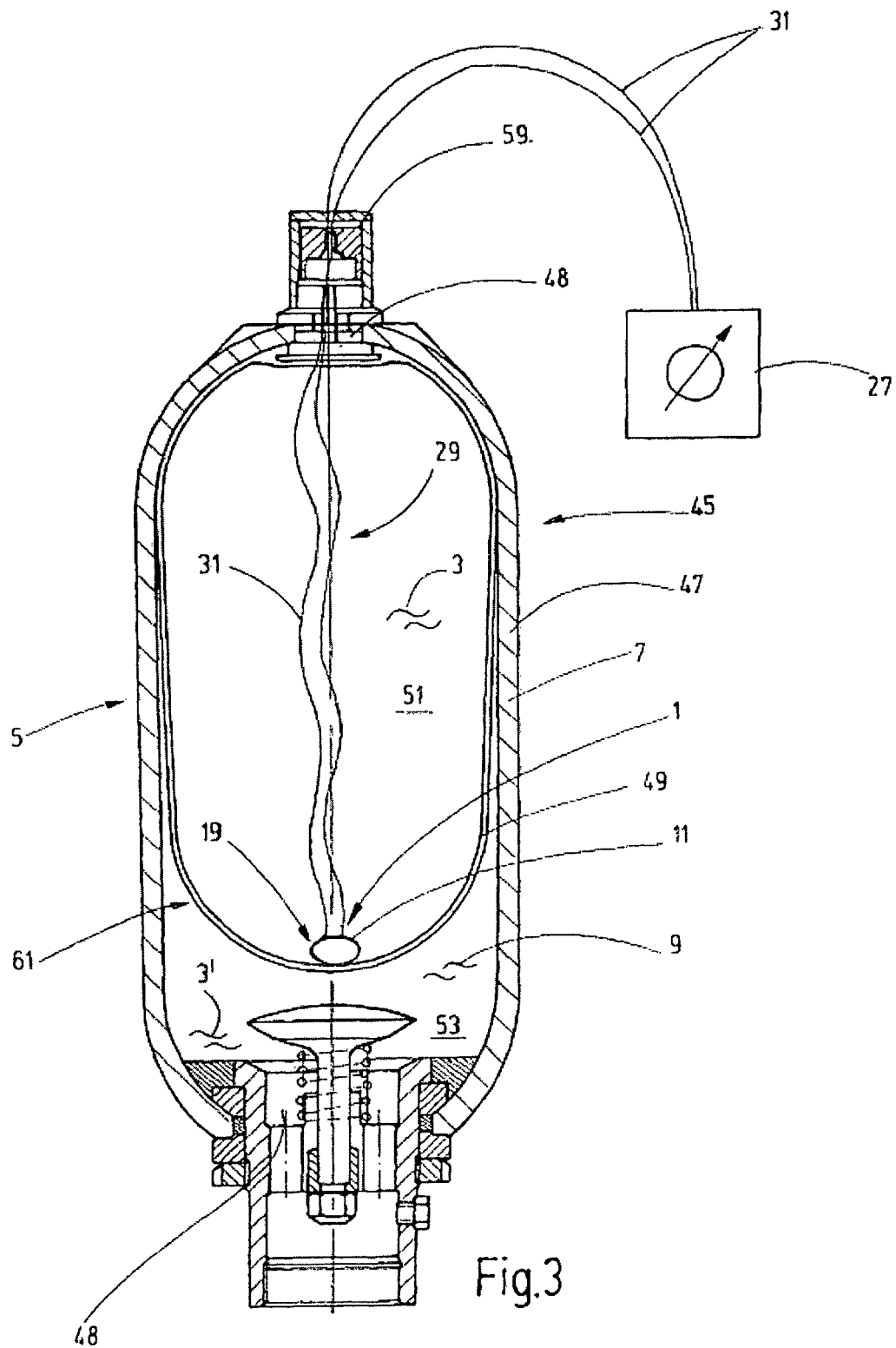
FIG. 3 is a schematic side view in section, not to scale, of a pressure device in the form of a hydraulic accumulator formed as a membrane accumulator with the sensor device of FIG. 1.

As FIGS. 1 and 3 show, merely by way of example, the measuring device 19 is connected to an evaluation device 27 by a data transmission path 29. In the exemplary embodiments shown, the data transmission path 29 takes the form of a cable connection 31 between the measuring device 19 and the evaluation device 27. FIG. 3 shows a cable connection 31 having at least one bipolar cable. In the exemplary embodiment shown in FIG. 3, the evaluation device 27 is disposed outside the pressure device 5.

FIG. 1 shows the oscillation device 13 formed in the manner of a reed switch 33. In the exemplary embodiment shown in FIG. 1, the reed switch 33 has two soft magnetic, elastic metal tongues 35, 35', which are diametrically opposite one another in the sensor element 11. The ends 57, 57' of the tongues axially overlap with a linear measurement of a. In the exemplary embodiment shown in FIG. 1, the ends 57, 57' of the metal tongues 35, 35' do not come into contact with one another. The metal tongues 35, 35' are essentially radially enclosed along the entire length thereof by the magnet device 21, which is formed as an electromagnetic solenoid 23. If the electromagnetic solenoid 23 is energized, a magnetic field 15, only schematically shown in FIG. 1, results. As the field strength increases, the metal tongues 35, 35' move towards one another. The metal tongues 35, 35' may come into contact with one another depending on the field strength of the magnetic field 15. In turn, when the field strength of the magnet device 21 decreases, the metal tongues 35, 35' move away from one another and are excited to produce oscillations. The energizing of the electromagnetic solenoid 23 can also be completely interrupted to initiate the oscillation process of the metal tongues 35, 35'. Instead of using an electromagnetic solenoid 23, a permanent magnet can also be used as a magnet device 21. To initiate an oscillation process in the metal tongues 35, 35', the permanent magnet is moved towards the sensor element 11 for example, until the metal tongues 35, 35' preferably come into contact with one another. The permanent magnet is subsequently moved away from the sensor element 11 so that the effect of the electromagnetic field of the permanent magnet on the sensor element 11 is thus reduced and the metal tongues 35, 35' separate from one another and preferably perform a free oscillation. Thus, a reed contact is created. One or more oscillation characteristics of the free oscillation of the metal tongues 35, 35' can be detected by the evaluation device 27. The reed switch 33 or the reed contact can then behave like a mechanical oscillator 55.

Figure 2:
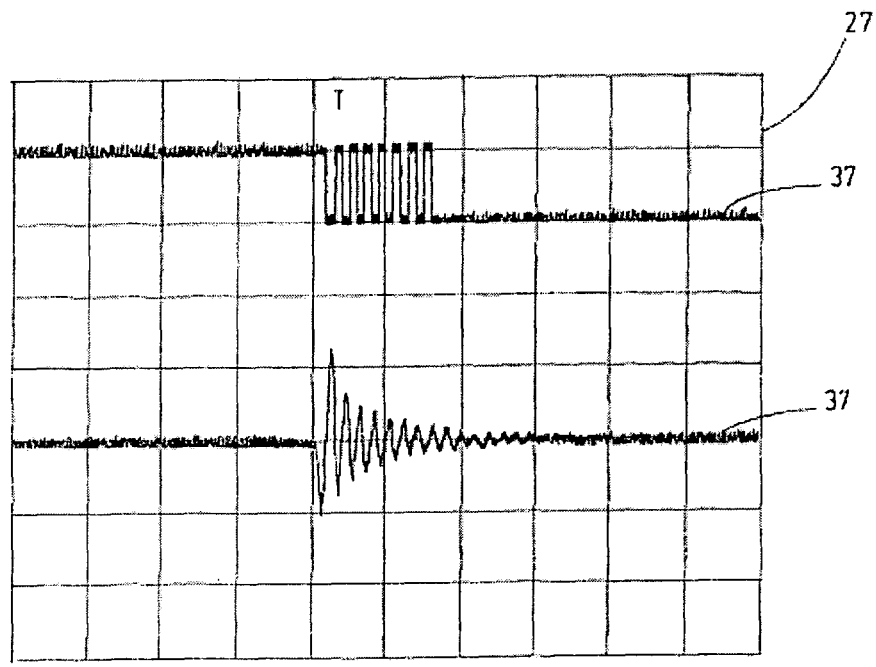
FIG. 2 is a graph of the progression of two oscillation characteristics during the detection of a flowable medium with the aid of the sensor device of FIG. 1.

As FIG. 2 shows, an oscillation characteristic 37 or multiple oscillation characteristics can hereby be detected by the measuring and evaluation device 19, 27. FIG. 2 shows two curve progressions, wherein, in the viewing direction of FIG. 2, the upper curve progression shows a number of oscillations of the sensor element 11 above a predeterminable threshold value of an oscillation amplitude. In the viewing direction of FIG. 2, the lower curve, on the other hand, shows an example that plots the absolute number of oscillations of the sensor element 11 over time. As FIG. 1 additionally shows, the sensor element 11 has a casing 39, which is preferably formed of an inorganic glass material.

The casing 39 encloses the metal tongues 35, 35' radially and axially, while maintaining a minimum radial distance from the metal tongues 35, 35'. The casing 39 of this type has two openings 41 for the influx of media to the metal tongue 35, 35'. The openings 41 may be placed in the casing 39 with an axial and radial spacing to one another. The oscillation characteristic 37 changes in a characteristic manner upon the influx of the respective medium 3, 3'. Thus the detection of a flowable medium 3 is enabled in an especially simple and cost-effective manner with the aid of the sensor device 1. In this case, the detection includes at least the detection of the type of flowable medium 3, 3'.

The sensor device 1 is principally designed in such a way that it is reusable even after the influx of media into the interior of the casing 39. Due to the simple design, the sensor element 11 can be produced very cost-effectively, and therefor, can also be used as a single-use sensor element 11, which can be replaced after an influx of media into the casing 39.

The energy for the operation of the sensor element 11 and of the measuring device 19 is provided by an electrical energy source 43 in the form of an accumulator, not described here in greater detail. In an embodiment of the data transmission path 29 in the form of a radio link, the energy for the operation of the sensor element 11 and of the measuring device 19 can also be obtained through an inductive coupling of the sensor element 11 and the measuring device 19 with an energy source of the evaluation device 27 or from energy of the medium 3, within the pressure device 5, such as from a difference in electrical potentials, from temperature differences in the medium 3, from the relative speed between the sensor element 11 and a flowing medium 3, or from pressure fluctuations in the medium.

In pressure devices 5, such as the pressure containers 7 shown in FIG. 3 or in a pressure line, at least one medium 3 present in the pressure device 5 can be detected by the sensor device 1 of the respective pressure device 5. The sensor device 1 can also be used to determine whether a flowable medium 3 is located in the pressure device 5. In addition, the sensor device 1 can be used to determine whether a medium 3 in is present in a media mixture, or the sensor device 1 can be used to detect the presence of a medium flow in a pressure device 5. Thus, for example, the filling level of a pressure container 7 and in general, the type of operating phase of a pressure device 5 of this type (a medium at rest or a medium in motion) can be determined. In this case, the detection of flowable media may include a comparison between the currently determined oscillation characteristic 37 and a number of characteristic oscillation characteristics stored in a memory of the evaluation device 27, each for different media 3, 3'.

FIG. 3 shows a pressure device 5 in the form of a hydraulic accumulator 45. The hydraulic accumulator 45 is formed as a bladder accumulator and is used to store fluid or gaseous media 3, 3', which may be under a pressure of up to 600 bar. An accumulator housing 47 of the hydraulic accumulator 45 is provided with connection openings 48 at both ends for media supply and discharge, to each of which connection openings valves are connected. The hydraulic accumulator 45 is formed substantially rotationally symmetrical, and extends along its longitudinal axis. The hydraulic accumulator 45 has a media chamber 51, which is separated from an additional media chamber 53 by a separator 49 in the form of an accumulator bladder 61 formed out of an elastomer material. A pressurized working gas is located in the media chamber 51 in the interior of the accumulator bladder 61. Located in the media chamber 53 outside the accumulator bladder 61, for example, is a hydraulic medium such as oil, which can be fed means of a hydraulic circuit and then retrieved from the media chamber 53. Further details about the pressure container 7 shown in FIG. 3 are not discussed here, since the pressure container 7 is already described in greater detail in a prior application by the applicant (DE 10 2006 004 120 A1).

In the exemplary embodiment of a pressure device 5, or of the pressure container 7, respectively, shown in FIG. 3, the evaluation device 27 of the sensor device 1 is present outside pressure device 5. The data transmission path 29 established between the evaluation device 27 and the sensor element 11 in the form of the cable connection 31 is guided through a supply valve 59. As shown, the sensor element 11 is located in a media chamber 51 sealed by a separator 49 that is formed as an accumulator bladder 61, and can be moved in the media chamber 51 to any location within the media chamber 51 during any operating phase of the pressure device 5 due to an excess length of the cable connection 31. The evaluation device 27 may include an output unit, which functions on an optical, acoustic or haptic basis, and in particular is capable of signaling to maintenance or operating personnel an inadvertent infiltration of a medium 3' from a media chamber 53 for the presently relative pressure device 5.

The measuring and evaluation device 19, 27 shown is able to carry out a nominal value compensation, which takes into account a current pressure in the media chamber 51 in which the sensor element 11 is located, and a current temperature in at least one of the media chambers 51, 53. Thus the impermeability of an accumulator bladder 61 can be established, preferably continuously, over the entire lifetime of said thereof with the aid of the sensor device 1 in addition to a measuring and evaluation device 19, 27. The sensor device and in particular the sensor element 11 are capable of detecting even the smallest transfer of media from the media chamber 53 outside the accumulator bladder 61 into the media chamber 51 within the accumulator bladder 61. For example, the infiltration of hydraulic oil or other material from the media chamber 53 through a point of failure in the accumulator bladder 61 and in the media chamber 51 can thus be detected even in the case of very small quantities.

While one embodiment has been chosen to illustrate the invention, it will be understood by those skilled in the art that various changes and modifications can be made therein without departing from the scope of the invention as defined in the claims.

The invention claimed is:

1. A sensor device for detecting flowable media received in a pressure device, comprising:
   a sensor element having an oscillation device excitable to produce oscillations under influence of a magnetic field and having an oscillation behavior changing upon influx of the media, said oscillation device including at least a reed switch or a reed contract;
   a field generation device producing the magnetic field and having a magnet device operatively connected to said sensor element;
   a measuring device detecting changes in the oscillation behavior and having an electromagnetic solenoid, said electromagnetic solenoid having magnetic flux influenced by oscillations of said sensor element in addition to an electric voltage in said electromagnetic solenoid when said sensor element is excited; and a casing receiving said sensor element and having a capillary opening in said casing for drawing the media by a capillary action of the media through said capillary opening and into an interior of said casing towards said sensor element.

2. A sensor device according to claim 1 wherein said casing is made of at least one plastic or glass material.

3. A sensor device according to claim 1 wherein said oscillation device comprises first and second magnetic and elastic tongues biased to move away from one another with decreasing field strength of said magnet device to be excited to produce the oscillations, at least one oscillation characteristic changing upon influx of the media into said casing to detect the media by said measuring device and an evaluation device.

4. A sensor device according to claim 1 wherein said measuring device is connected to an evaluation device located outside of a pressure device in which said sensor element is located by a data transmission path, said data transmission path being at least one of a cable connection or a radio link.

5. A sensor device according to claim 4 wherein said measuring and evaluation devices are capable of determining at least one of an absolute number of oscillations of said sensor element or a number of oscillations above a predeterminable threshold value of an oscillation amplitude as a function of media that is detected.

6. A sensor device according to claim 1 wherein an accumulator supplies operational energy to said at least one of said sensor element and said measuring device.

7. A sensor device according to claim 6 wherein said accumulator is a battery.

8. A sensor device according to claim 1 wherein an energy source of an evaluation device is inductively coupled to said sensor element and said measuring device.

9. A sensor device according to claim 1 wherein energy of a medium within a pressure device is supplied to at least one of said sensor element or said measuring device.

10. A sensor device according to claim 9 wherein said energy is from at least one of a difference in electrical potentials, temperature differences, relative speed between said sensor element and a flowing media or pressure fluctuations in the media.

11. A pressure device according to claim 10 wherein an evaluation device is connected to said sensor element via a data transmission path.

12. A pressure device according to claim 10 wherein said evaluation device is located outside of one of said pressure container or pressure line.

13. A pressure device according to claim 11 wherein said evaluation device is on said sensor device.

14. A pressure device according to claim 11 wherein said data transmission path is at least one of a cable connection or a radio link.

15. A pressure device, comprising:
at least one of a pressure container or a pressure line with a flowable medium therein; and
a sensor device in said at least one pressure container or pressure line detecting at least one of a pressure or absence of the medium or of a medium flow or of a medium in a media mixture, the sensor device including
a sensor element having an oscillation device excitable to produce oscillations under influence of a magnetic field and having an oscillation behavior changing upon influx of the media, said oscillation device including at least a reed switch or a reed contract,
a field generation device producing the magnetic field and having a magnet device operatively connected to said sensor element,
a measuring device detecting changes in the oscillation behavior and having an electromagnetic solenoid, said electromagnetic solenoid having magnetic flux influenced by oscillations of said sensor element in addition to an electric voltage in said electromagnetic solenoid when said sensor element is excited, and
a casing receiving said sensor element and having a capillary opening in said casing for drawing the media by a capillary action of the media through said capillary opening and into an interior of said casing towards said sensor element.

16. A pressure device according to claim 15 wherein said at least one of pressure container or pressure line is a hydraulic accumulator having a separator movably disposed in an accumulator housing of said hydraulic accumulator and separating two adjacently disposed first and second media chambers within said accumulator housing, two media different from one another being in the respective media chambers; and
said sensor device is in said first media chamber, and registers and signals an inadvertent flow of the media of said second media chamber into first media chamber.

17. A measuring method for operating a sensor device in a pressure device, comprising the steps of:
providing a sensor device in the pressure device with the sensor device including a sensor element, a field generation device, a measuring device and a casing, the sensor device having an oscillation device excitable to produce oscillations under influence of a magnetic field and having an oscillation behavior changing upon influx of the media, the oscillation device including at least a reed switch or a reed contract, the field generation device producing the magnetic field and having a magnet device operatively connected to the sensor element, the measuring device detecting changes in the oscillation behavior and having an electromagnetic solenoid, the electromagnetic solenoid having magnetic flux influenced by oscillations of the sensor element in addition to an electric voltage in the electromagnetic solenoid when the sensor element is excited, the casing receiving the sensor element and having a capillary opening in the casing that draws the media by a capillary action of the media through the capillary opening and into an interior of the casing towards the sensor element;
operating the reed switch or reed contact to behave as a mechanical oscillator under the magnet field of the magnet device;
registering changes in the oscillation behavior of the reed switch or reed contact by the measuring device upon the influx of the media; and
relaying measured data by the measuring device to an evaluation device for further evaluation.

18. A measuring method according to claim 17 wherein the measuring and evaluation devices perform a nominal value compensation accounting for a current pressure in a media chamber of the pressure device in which the sensor element is mounted and for a current temperature in the media chamber.

* * * * *